United States Patent
Kim et al.

(10) Patent No.: US 10,888,402 B2
(45) Date of Patent: *Jan. 12, 2021

(54) MOBILE LINKED IMPLANT DIAGNOSIS SYSTEM

(71) Applicants: MEGAGEN IMPLANT CO., LTD., Daegu (KR); Jong Cheol Kim, Daegu (KR)

(72) Inventors: Jong Cheol Kim, Daegu (KR); Kwang Bum Park, Daegu (KR)

(73) Assignees: MEGAGEN IMPLANT CO., LTD.; Jong Cheol Kim

( * ) Notice: Subject to any disclaimer, the term of this patent is extended or adjusted under 35 U.S.C. 154(b) by 0 days.

This patent is subject to a terminal disclaimer.

(21) Appl. No.: 16/340,097

(22) PCT Filed: Jan. 10, 2017

(86) PCT No.: PCT/KR2017/000331
§ 371 (c)(1),
(2) Date: Apr. 5, 2019

(87) PCT Pub. No.: WO2018/066765
PCT Pub. Date: Apr. 12, 2018

(65) Prior Publication Data
US 2020/0046473 A1    Feb. 13, 2020

(30) Foreign Application Priority Data
Oct. 6, 2016 (KR) .................. 10-2016-0129286

(51) Int. Cl.
*A61C 13/00* (2006.01)
*G06T 7/33* (2017.01)
(Continued)

(52) U.S. Cl.
CPC ............ *A61C 13/0004* (2013.01); *G06T 7/33* (2017.01); *G06T 19/20* (2013.01);
(Continued)

(58) Field of Classification Search
None
See application file for complete search history.

(56) References Cited

U.S. PATENT DOCUMENTS 8,548,778 B1    10/2013    Hart et al.
2010/0292963 A1*  11/2010  Schroeder ............... G06F 30/20
                                                         703/1
(Continued)

FOREIGN PATENT DOCUMENTS

EP    1036543 A1    9/2000
EP    2742857 A1    6/2014
(Continued)

OTHER PUBLICATIONS

Extended European Search Report for Application No. 17858560.0 dated Feb. 18, 2020.
(Continued)

*Primary Examiner* — Yingchun He
(74) *Attorney, Agent, or Firm* — Renaissance IP Law Group LLP

(57) ABSTRACT

A mobile linked implant diagnosis system includes an implant diagnosis apparatus acquiring synthetic three-dimensional (3D) image data about a mouth area of a target patient and generating implant surgery planning data, in which virtual implant data is overlapped on the synthetic 3D image data, based on the synthetic 3D image data, a server apparatus connected to the implant diagnosis apparatus in a wired or wireless manner, and receiving information of interest that is part of the implant surgery planning data generated in the implant diagnosis apparatus and storing the (Continued)

information of interest, and a mobile device connected to the server apparatus in a wired or wireless manner, and receiving the information of interest from the server apparatus and displaying the information of interest. The information of interest comprises partial 3D image data of the implant surgery data, the partial 3D image data being data about a preset area around the virtual implant.

12 Claims, 13 Drawing Sheets

(51) Int. Cl.
| | |
|---|---|
| *G06T 19/20* | (2011.01) |
| *A61B 34/00* | (2016.01) |
| *A61B 6/00* | (2006.01) |
| *A61B 34/10* | (2016.01) |
| *H04M 1/725* | (2006.01) |
| *A61B 5/00* | (2006.01) |

(52) U.S. Cl.
CPC ............... *G06T 2200/24* (2013.01); *G06T 2207/20221* (2013.01); *G06T 2207/30036* (2013.01); *G06T 2207/30052* (2013.01); *G06T 2207/30204* (2013.01); *G06T 2219/008* (2013.01); *G06T 2219/028* (2013.01); *G06T 2219/2004* (2013.01)

(56) References Cited

U.S. PATENT DOCUMENTS

| | | | |
|---|---|---|---|
| 2013/0172731 A1* | 7/2013 | Gole | A61B 5/7425 |
| | | | 600/424 |
| 2015/0091778 A1* | 4/2015 | Day | G16H 40/63 |
| | | | 345/1.3 |
| 2015/0265372 A1 | 9/2015 | Kim et al. | |
| 2015/0379780 A1 | 12/2015 | Jin | |
| 2016/0287336 A1* | 10/2016 | Kim | G06T 7/0012 |

FOREIGN PATENT DOCUMENTS

| | | | |
|---|---|---|---|
| EP | 2929854 A2 | 10/2015 | |
| EP | 3075344 A1 | 10/2016 | |
| JP | 2003245289 A | 9/2003 | |
| JP | 2009501036 A | 1/2009 | |
| JP | 2015066433 A | 4/2015 | |
| KR | 20140111902 A | 9/2014 | |
| KR | 101544773 B1 | 8/2015 | |
| KR | 101554157 B1 * | 9/2015 | |
| KR | 101554157 B1 | 9/2015 | |
| KR | 20160002703 A | 1/2016 | |
| WO | 2016148297 A1 | 9/2016 | |

OTHER PUBLICATIONS

Extended European Search Report for Application No. 17858560.0 dated May 27, 2020.

* cited by examiner

MOBILE LINKED IMPLANT DIAGNOSIS SYSTEM

TECHNICAL FIELD

The inventive concept relates to a mobile linked implant diagnosis system, and more particularly, to a mobile linked implant diagnosis system which may enable a user to review information about implant surgery planning not only at a fixed position such as on a desktop personal computer (PC), but also on a mobile device conveniently.

BACKGROUND ART

An implant originally means a substitute used to restore lost human tissues. In a dental field, however, the implant refers to a series of procedures to transplant an artificial tooth.

To replace a lost dental root, the implant is a series of dental procedures to restore the function of a tooth by placing a fixture, which is a dental root formed of titanium and having no rejection to a human body, in an alveolar bone where a tooth is lost, and then fixing an artificial tooth thereto.

In the case of a general prosthesis or denture, surrounding teeth or bones may be damaged as time passes. In contrast, since the implant does not harm the surrounding tooth tissues, provides the same function and shape as a natural tooth, and has no tooth decay, the implant may be used semi-permanently.

In an artificial tooth surgery (referred to as an implant or an implant surgery), a implantation hole is formed by using a drill, which varies according to the type of a fixture, the fixture is placed in the alveolar bone and has osseointegration with the bone, and an abutment is coupled to the fixture and crowned with a final prosthesis.

The implant as above may facilitate restoration of a single missing tooth, enhance the function of a denture for partially toothless and fully toothless patients, improve an aesthetic aspect of dental prosthesis restoration, and furthermore distribute excessive stress applied to surrounding support bone tissues and stabilize a row of teeth.

The dental implant may generally include a fixture placed as an artificial tooth root, an abutment coupled to the fixture, an abutment screw to fix the abutment to the fixture, and an artificial tooth coupled to the abutment. Before the abutment is coupled to the fixture, that is, during a period of osseointegration of the fixture to the alveolar bone, the abutment is coupled to the fixture and a coupling state is maintained.

The fixture, which is one of components of a dental implant, is a portion placed in a drill hole formed in the alveolar bone by using a drill and functions as an artificial tooth root. Accordingly, the fixture is firmly placed in the alveolar bone.

The placement of an implant differs much according to patients because an implant placement position is determined according to various factors such as a patient's tooth state, the position of a tooth requiring implant surgery, or a state of a patient's alveolar bone.

In particular, the bone density of the alveolar bone is a very important factor in the placement of an implant, and the position, depth, and direction of the placement of an implant are carefully determined according to the state of the bone density of a patient.

As described above, conventionally, since the placement of an implant differs much according to patients, an implant diagnosis system has been developed, which assists the medical doctor to accurately recognize such a difference and establish a simulation surgery and surgery planning.

A conventional implant diagnosis system enables identification of optimal position and angle of the placement of an implant by overlapping a virtual implant on three-dimensional (3D) image data including the position and bone density of a bone and a tooth of a mouth area of a patient.

The implant diagnosis system requires a high-performance computer to process 3D image data and thus a desktop PC is mainly used as the high-performance computer.

Thus, implant surgery planning data, in which an optimal position and an optimal angle of the placement of an implant are indicated, is generated in a high-performance desktop PC, and the generated implant surgery planning data is reviewed on the high-performance desktop PC.

However, for dental doctors hampered by an insufficient treatment time, it is quite difficult in terms of time to visit a diagnosis center equipped with desktop PCs to review the implant surgery planning data In particular, since it is a waste of time for dental doctors to visit the diagnosis center merely to check a simple matter, a demand for a mobile linked implant diagnosis system, which enables the dental doctors to conveniently review the implant surgery planning data through smartphones in transportations or in extra break time, has increased.

To meet the above demands, conventionally, a mobile linked implant diagnosis system by which implant surgery planning data may be simply reviewed through smartphones has been suggested. In the conventional mobile linked implant diagnosis system, the information provided to a mobile device is merely an image file (2D image file) of surgery planning, not 3D image data such as computed tomography (CT) data.

In other words, since the mobile device having a limited performance is difficult to handle the 3D image data that is large data and thus a 2D file, for example, a JPG file, is generated from a 3D file and provided to the mobile device, only a 2D image file of the implant surgery planning data is provide to the mobile device.

However, in the conventional mobile linked implant diagnosis system, since the 2D image of the implant surgery planning data provided to the mobile device is merely an image, the dental doctor is unable to correct even a little portion of implant surgery planning in the mobile device, for example, correcting one fixture to another or finely changing a placement angle of an implant. Accordingly, under the convention mobile linked implant diagnosis system, it is a problem that the dental doctor is quite difficult to conduct a meaningful surgery planning review in the mobile device.

DISCLOSURE

Technical Problem

The inventive concept provides a mobile linked implant diagnosis system which enables a user to correct implant surgery planning in a mobile device.

Technical Solution

According to an aspect of the inventive concept, there is provided a mobile linked implant diagnosis system including an implant diagnosis apparatus acquiring synthetic three-dimensional (3D) image data about a mouth area of a target patient and generating implant surgery planning data, in which virtual implant data is overlapped on the synthetic 3D image data, based on the synthetic 3D image data, a server apparatus connected to the implant diagnosis apparatus in a wired or wireless manner, and receiving information of interest that is part of the implant surgery planning data generated in the implant diagnosis apparatus and storing the information of interest, and a mobile device connected to the server apparatus in a wired or wireless manner, and receiving the information of interest from the server apparatus and displaying the information of interest, in which the information of interest comprises partial 3D image data of the implant surgery data, the partial 3D image data being data about a preset area around the virtual implant.

The partial 3D image data may include the implant surgery planning data in a boundary area spaced apart by a preset distance from a center of the virtual implant.

The boundary area may be provided in a hexahedral shape.

The boundary area in a hexahedral shape may have a length in a first axis direction of about 15 mm to about 45 mm, a length in a second axis direction of about 15 mm to about 45 mm, and a length in a third axis direction of about 20 mm to about 60 mm, The mobile device may include a smartphone or a handheld terminal.

The mobile device may include a mobile device display unit displaying the partial 3D image data, a mobile device input unit receiving an input of information from a user, and a mobile device operation unit electrically connected to the mobile device input unit and correcting the partial 3D image data according to information input from the user.

The mobile device display unit may section a screen provided to the user into a plurality of divided areas, and the divided areas may include a first area, in which a plane image obtained by cutting the partial 3D image data along a first axis and a second axis crossing the first axis, is displayed, a second area, in which a plane image obtained by cutting the partial 3D image data along the second axis and a third axis crossing the second axis, is displayed; and a third area, in which a plane image obtained by cutting the partial 3D image data along the first axis and the third axis, is displayed.

The mobile device display unit may visually display bone density in the first area to third area.

The mobile device display unit may visually display bone density in a preset area in the first area to third area.

The bone density may be displayed in a different color according to a value of the bone density.

The color may be a chromatic color.

The divided areas may further include a fourth area in which 3D image data obtained by overlapping the virtual implant to second 3D image data acquired by scanning plaster patterns of teeth of the target patient is displayed.

The implant diagnosis apparatus may include a first image information acquirement apparatus acquiring first 3D image data about the mouth area of the target patient, a second image information acquirement apparatus acquiring second 3D image data by scanning plaster patterns of teeth of the target patient, and a data processing apparatus receiving and matching the first 3D image data and the second 3D image data and generating the synthetic 3D image data, and generating surgery planning data based on the synthetic 3D image data.

The plaster patterns of teeth may be provided with a matching reference marker for matching the first 3D image data and the second 3D image data.

The matching reference marker may be provided plurally, and the plurality of matching reference markers may be arranged spaced apart from one another.

The data processing apparatus may include an input unit receiving information from a user, an operation unit generating the synthetic 3D image data, electrically connected to the input unit, and correcting the synthetic 3D image data based on the information input from the user, and a display unit electrically connected to the operation unit and visually displaying the synthetic 3D image data.

The data processing apparatus may generate the synthetic 3D image data by performing a pre-matching operation of pre-matching the first 3D image data and the second 3D image data based on the coordinate of the matching reference marker of the second 3D image data and then performing a precise matching operation of precisely matching the second 3D image data to the first 3D image data in the pre-matched synthetic 3D image data.

In the pre-matching operation, the operation unit may section a display area of the display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed, receive an input of the coordinate of the matching reference marker in the second 3D image data display zone through the input unit, receive an input of a virtual coordinate corresponding to the coordinate of the matching reference marker in the teeth area display zone through the input unit, and display the pre-matched synthetic 3D image data in the synthetic 3D image data display zone by matching the input coordinate of the matching reference marker G2 and the input virtual coordinate.

In the precise matching operation, the operation unit may section the display area of the display unit into a plurality of divided zones, arrange different plane images of the pre-matched synthetic 3D image data in the plurality of divided zones, and receive an input of a state of matching the second 3D image data to the first 3D image data in each divided zone through the input unit.

The plurality of divided zones may include a first area in which a plane image obtained by cutting the pre-matched synthetic 3D image data along a first axis and a second axis crossing the first axis is displayed, a second area in which a plane image obtained by cutting the pre-matched synthetic 3D image data along the second axis and a third axis crossing the second axis at a position of a first movement point displayed in the first area is displayed, a third area in which a plane image obtained by cutting the pre-matched synthetic 3D image data along the first axis and the third axis at the position of the first movement point displayed in the first area is displayed, a fourth area in which a plane image obtained by cutting the pre-matched synthetic 3D image data along the second axis and the third axis at a position of a second movement point displayed in the first area is displayed, a fifth area in which a plane image obtained by cutting the pre-matched synthetic 3D image data along the first axis and the third axis at the position of the second movement point displayed in the first area is displayed, and a sixth area in which a plane image obtained by cutting the pre-matched synthetic 3D image data along the second axis and the third axis at a position of a third movement point displayed in the first area is displayed.

The first to third movement points may be movable by an operation of the user, the images of the second area and the third area are changed linked with a movement of the first movement point, the images of the fourth area and the fifth area are changed linked with a movement of the second movement point, and the image of the sixth area is changed linked with a movement of the third movement point.

When a virtual fixture to be placed in the target patient is overlapped on the synthetic 3D image data, the data processing apparatus may visually display bone density around the virtual fixture based on the virtual fixture.

The data processing apparatus may visually display bone density of an area in contact with an outer contour of the virtual fixture.

The bone density around the virtual fixture may be displayed in a different color according to a value of the bone density.

Advantageous Effects

According to the exemplary embodiments of the present invention, since only the partial 3D image data of the implant surgery data, which is the 3D image data around the virtual implant K, is provided to the mobile device 300, the user may correct the partial 3D image data around the virtual implant K that is a user's main interest, for example, a correction of changing one fixture to another, a correction of finely changing an implant placement angle, etc., through the mobile device 300 within the specifications of the mobile device 300.

MODES OF THE INVENTION

Figure 1:
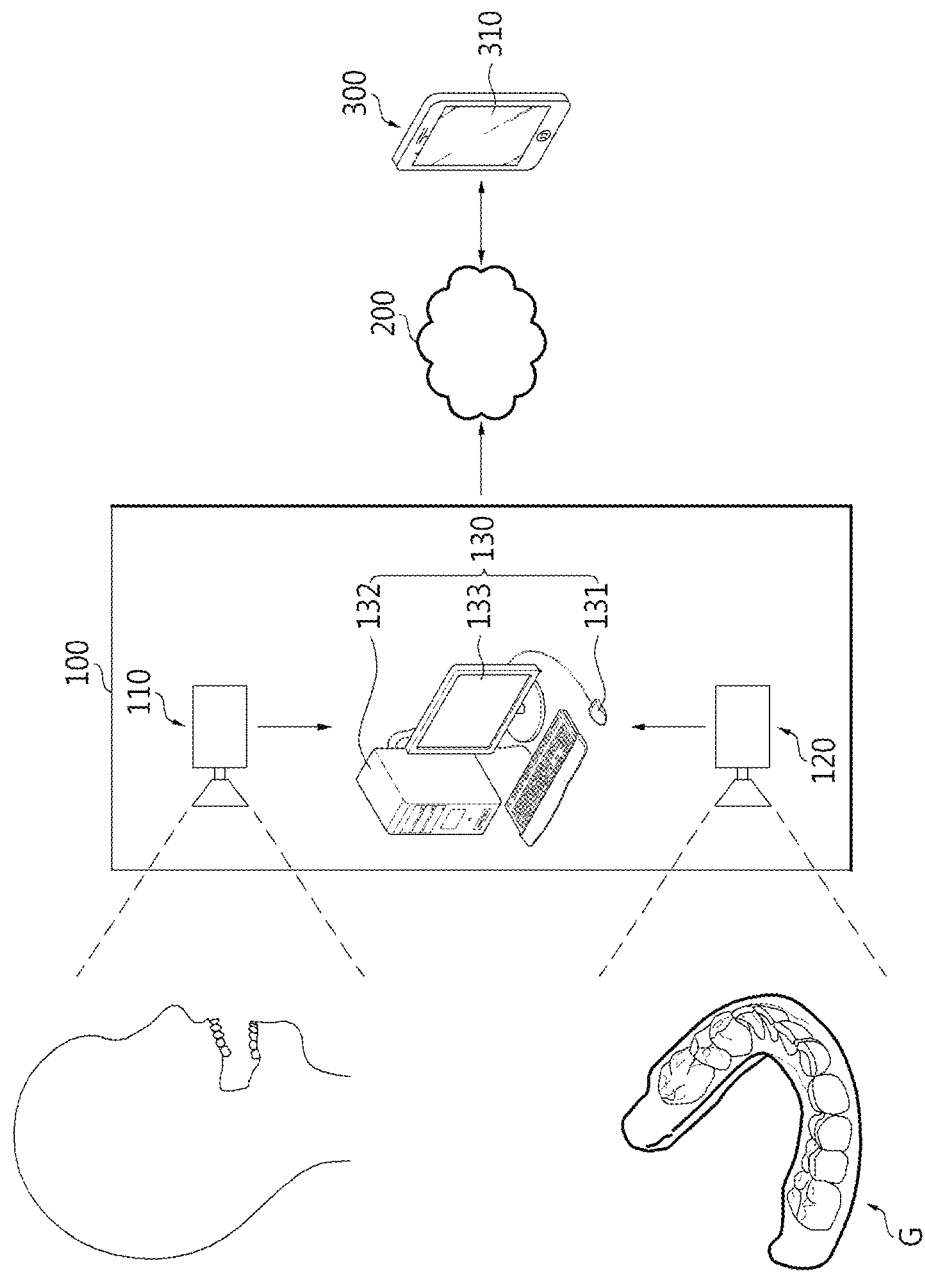
FIG. 1 illustrates a mobile linked implant diagnosis system according to an embodiment.

The attached drawings for illustrating exemplary embodiments of the inventive concept are referred to in order to gain a sufficient understanding of the inventive concept and the merits thereof.

Hereinafter, the inventive concept will be described in detail by explaining exemplary embodiments of the inventive concept with reference to the attached drawings. Like reference numerals in the drawings denote like elements.

In the following description, a first axis, a second axis, and a third axis denote an X-axis, a Y-axis, and a Z-axis, respectively.

Figure 2:
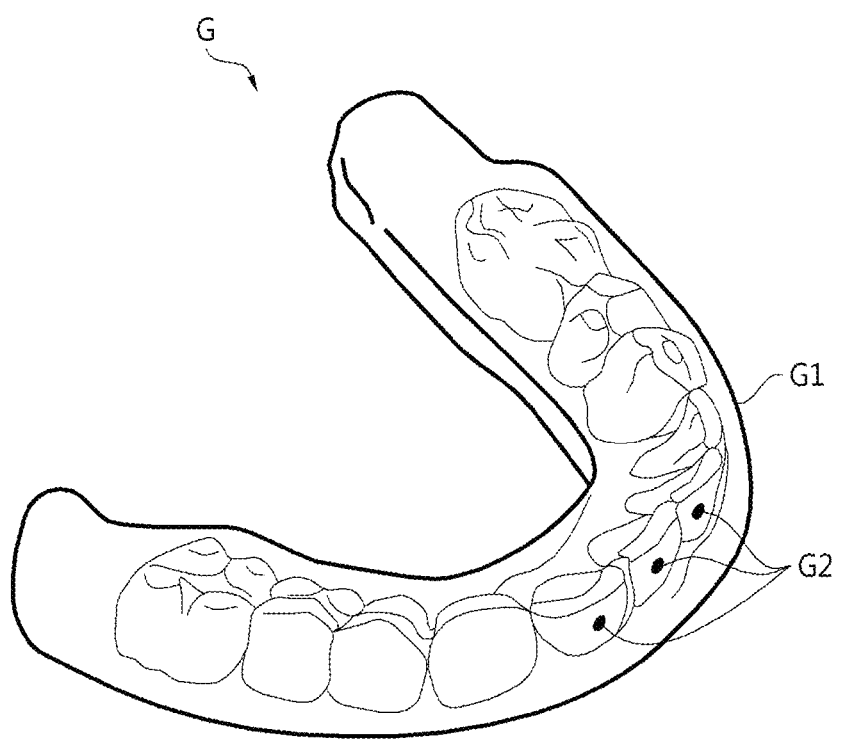
FIG. 2 illustrates the plaster patterns of teeth of FIG. 1.
Figure 3:
FIGS. 3 and 4 are images visually displaying hone density around a virtual fixture on a display unit of FIG. 1.
Figure 4:
Figure 5:
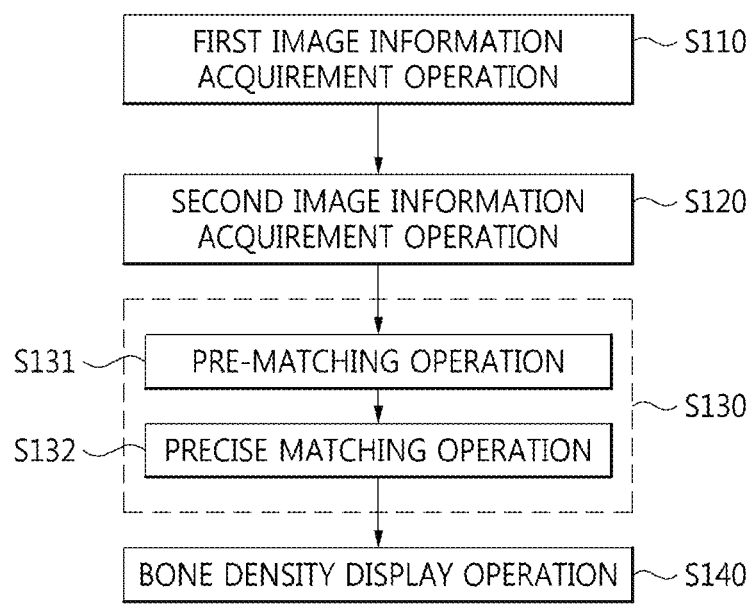
FIG. 5 is a flowchart of a method of generating an image for implant diagnosis according to the mobile linked implant diagnosis system of FIG. 1.
Figure 6:
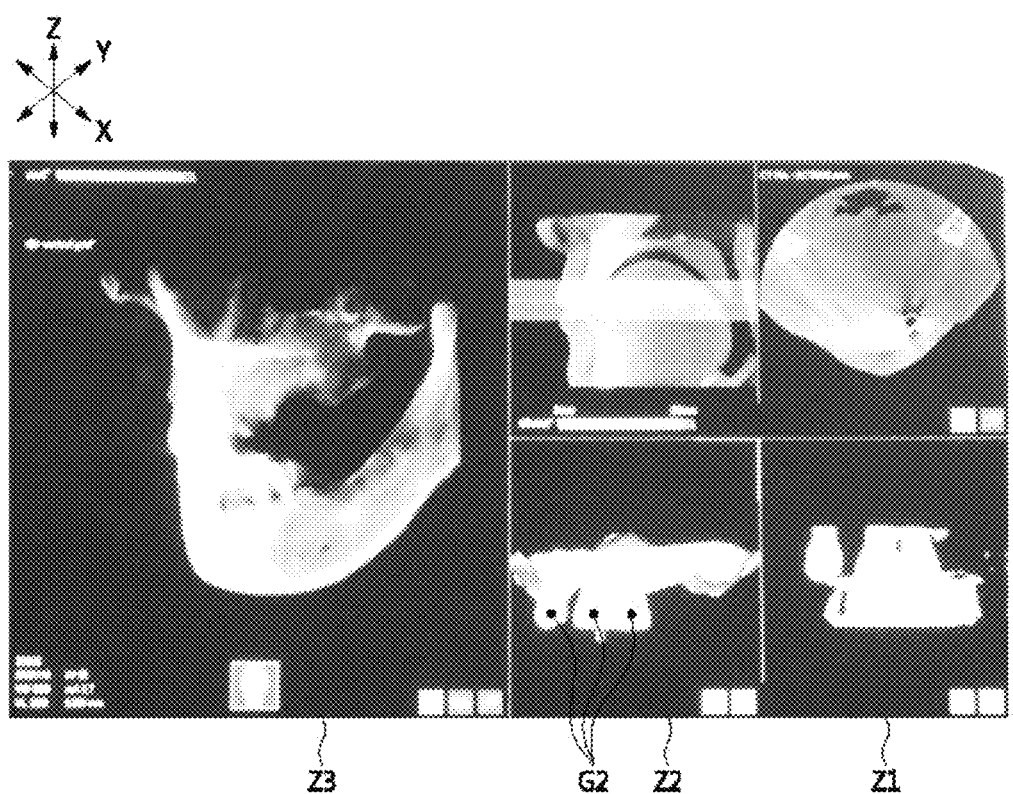
FIGS. 6 and 7 are images of the display unit in a pre-matching operation of the synthetic 3D image data acquirement operation of FIG. 5.
Figure 7:
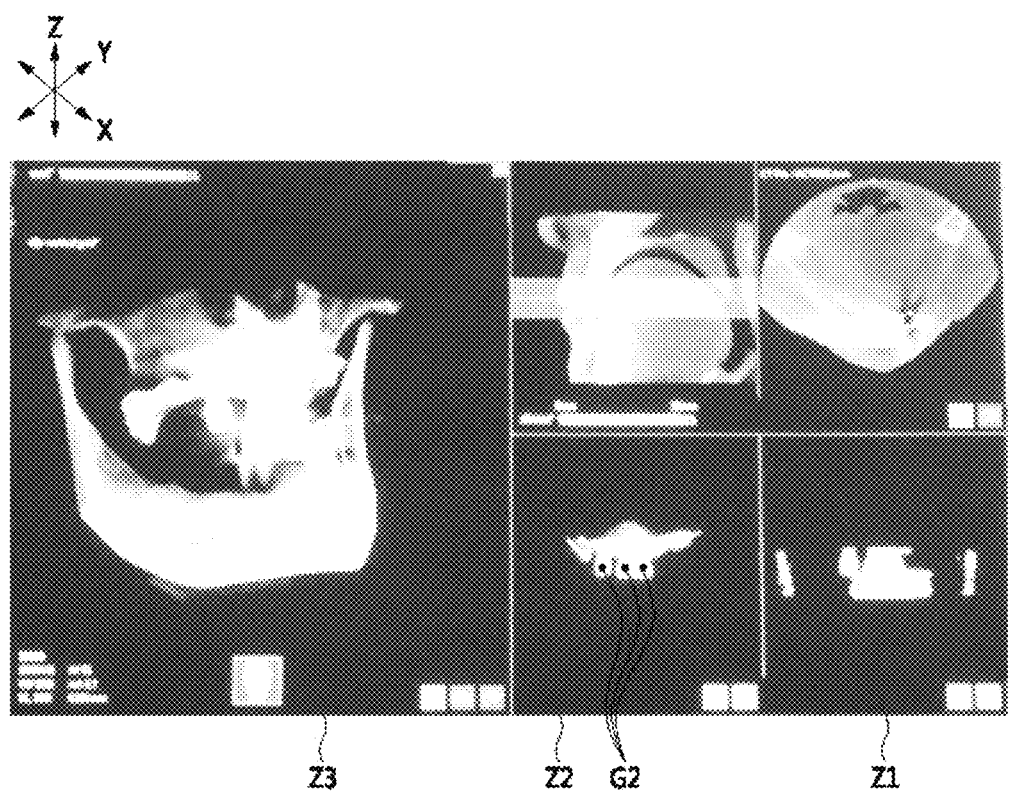
Figure 8:
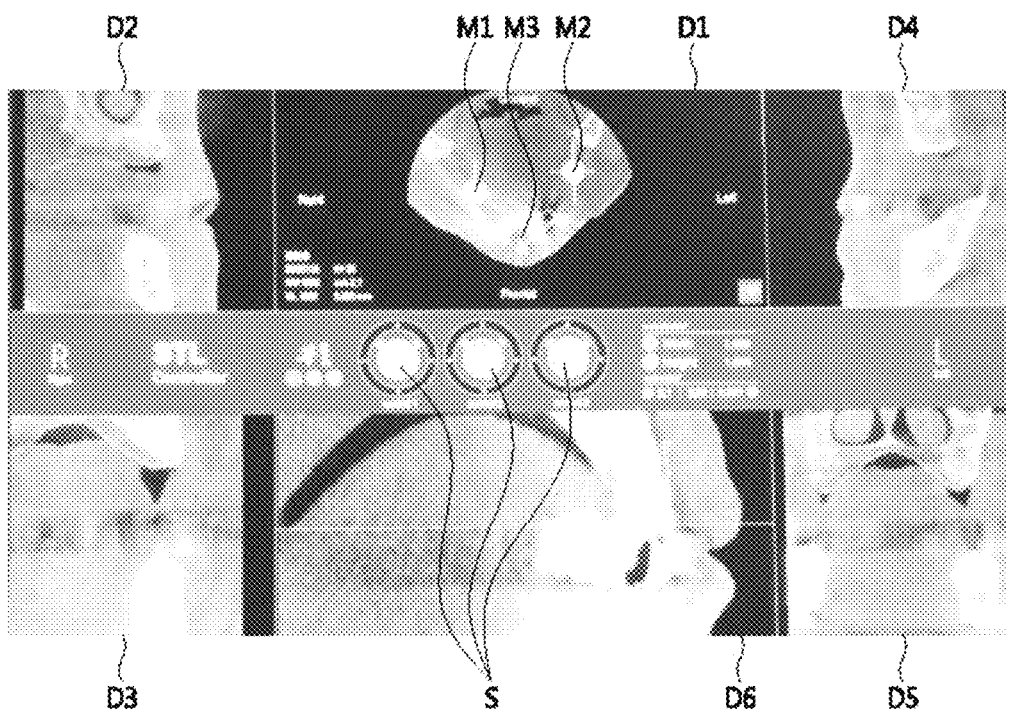
FIGS. 8 and 9 are images of the display unit in a precise matching operation of the synthetic 3D image data acquirement operation of FIG. 5.
Figure 9:
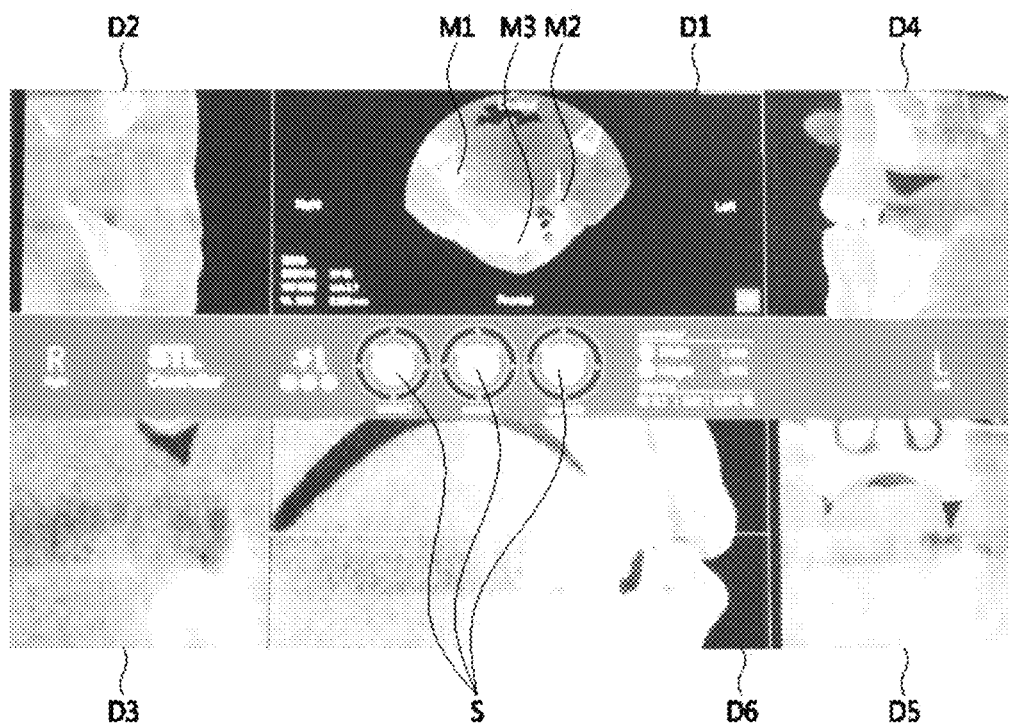
Figure 10:
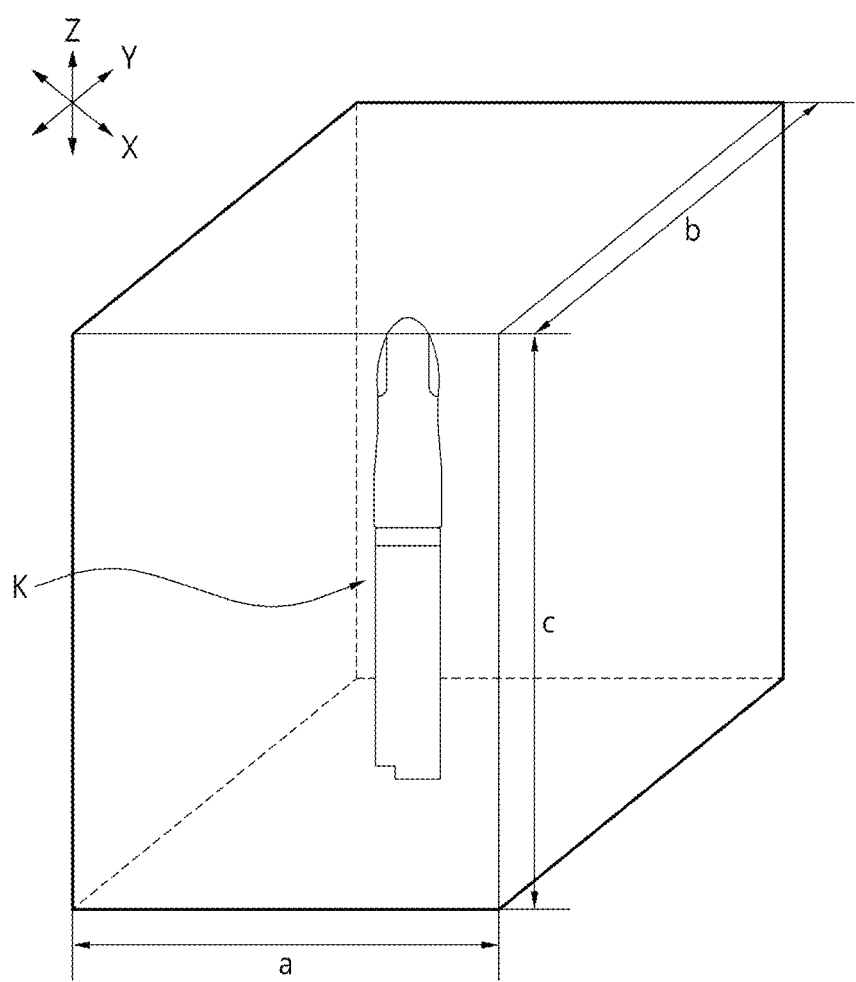
FIG. 10 is a perspective view illustrating a boundary area of a partial 3D image data transmitted to the server apparatus of FIG. 1.
Figure 11:
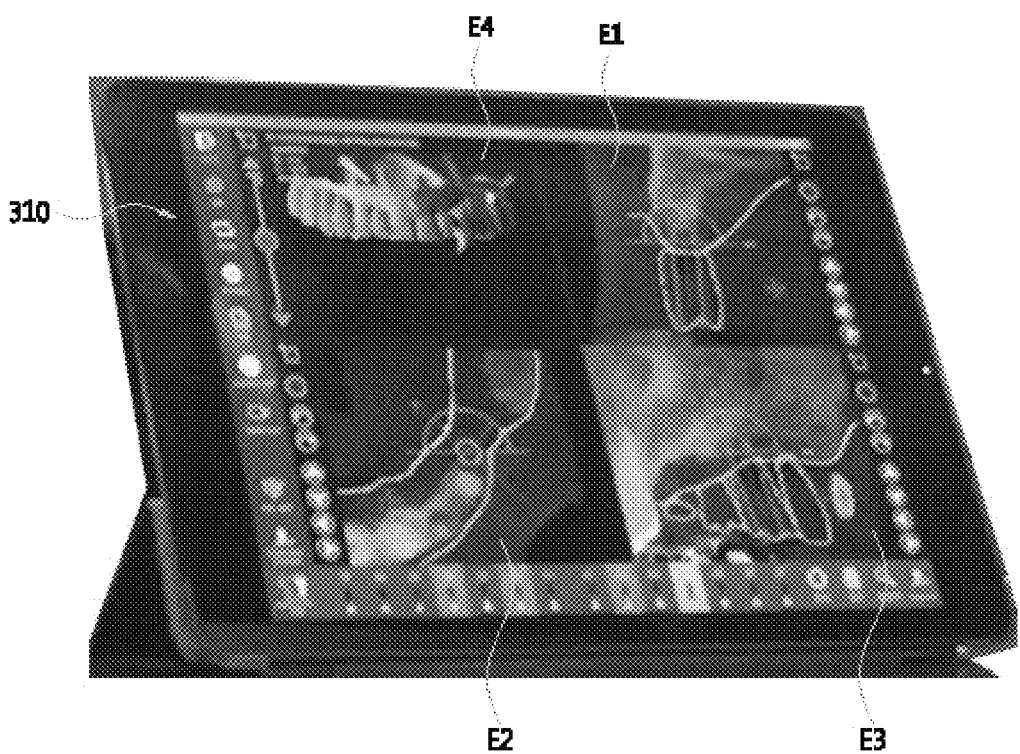
FIGS. 11 and 12 are screens displayed in the mobile device of FIG. 1.
Figure 12:
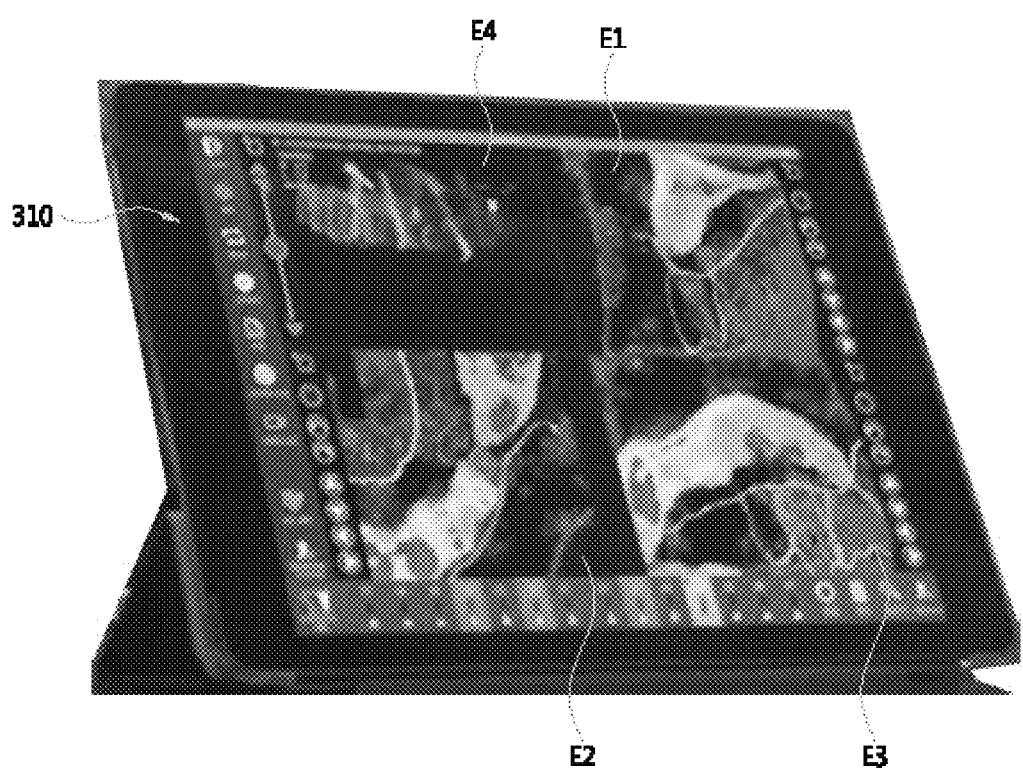

FIG. 1 illustrates a mobile linked implant diagnosis system according to an embodiment. FIG. 2 illustrates the plaster patterns of teeth of FIG. 1. FIGS. 3 and 4 are images visually displaying hone density around a virtual fixture on a display unit of FIG. 1. FIG. 5 is a flowchart of a method of generating an image for implant diagnosis according to the mobile linked implant diagnosis system of FIG. 1. FIGS. 6 and 7 are images of the display unit in a pre-matching operation of the synthetic three-dimensional (3D) image data acquirement operation of FIG. 5. FIGS. 8 and 9 are images of the display unit in a precise matching operation of the synthetic 3D image data acquirement operation of FIG. 5. FIG. 10 is a perspective view illustrating a boundary area of a partial 3D image data transmitted to the server apparatus of FIG. 1. FIGS. 11 and 12 are screens displayed in the mobile device of FIG. 1.

The mobile linked implant diagnosis system according to the present embodiment, as illustrated in FIG. 1, may include an implant diagnosis apparatus 100 for acquiring synthetic 3D image data about a mouth area of the target patient and generating implant surgery planning data obtained by overlapping virtual implant K data on the synthetic 3D image data based on the synthetic 3D image data, a server apparatus 200 connected to the implant diagnosis apparatus 100 in a wired or wireless manner and receiving and storing information of interest that is part of the implant surgery planning data generated in the implant diagnosis apparatus 100, and a mobile device 300 connected to the server apparatus 200 in a wired or wireless manner and receiving the information of interest from the server apparatus 200 and displaying the received information of interest.

The implant diagnosis apparatus 100 acquires the synthetic 3D image data about the mouth area of the target patient, and generates the implant surgery planning data in which the virtual implant K data is overlapped on the synthetic 3D image data based on the synthetic 3D image data.

The mobile linked implant diagnosis system 100 according to the present embodiment may include a first image information acquirement apparatus 110 for obtaining first 3D image data about a mouth area of a target patient, a second image information acquirement apparatus 120 for obtaining second 3D image data by scanning plaster patterns of teeth G of the target patient, and a data processing apparatus 130 for receiving and matching the first 3D image data and the second 3D image data to generate synthetic 3D image data.

The first image information acquirement apparatus 110 acquires the first 3D image data about the mouth area of the target patient. The first image information acquirement apparatus 110 of the present embodiment may include computed tomography (CT) and the first 3D image data of the present embodiment signifies a 3D image implemented by using a plurality of sectional images, but the present inventive concept is not limited thereto and a variety of imaging apparatuses such as an magnetic resonance imaging apparatus may be used as the first image information acquirement apparatus 110 of the present embodiment.

The second image information acquirement apparatus 120 acquires second 3D image data by scanning the plaster patterns of teeth G of the target patient.

The plaster patterns of teeth G of the present embodiment are formed in a shape of teeth and gum of the target patient. After a tray with an impression material is inserted in the mouth of the target patient, the teeth of the target patient press the impression material and thus the plaster patterns of teeth G are manufactured in a shape of impressed teeth and surrounding gum.

The plaster patterns of teeth G of the present embodiment are provided with a matching reference marker G2 for matching the first 3D image data and the second 3D image data.

The matching reference marker G2 is used as a reference coordinate for the matching of the first 3D image data and the second 3D image data. The matching reference marker G2 may be used when the data processing apparatus 130 generates synthetic 3D image data by matching a coordinate of the matching reference marker G2 of the second 3D image data and a coordinate of a virtual position corresponding to the matching reference marker G2 in the first 3D image data.

The matching reference marker G2 of the present embodiment is provided plurally and the plurality of matching reference markers G2 are arranged spaced apart from one another. In the present embodiment, at least three matching reference markers G2 are provided and the at least three matching reference markers G2 are arranged spaced apart from one another.

The matching reference marker G2 is formed in a structure or material to be distinguished from plaster patterns of teeth main body G1 in the second 3D image data.

The second image information acquirement apparatus 120 may include a 3D scanner (not shown) that acquires the second 3D image data by scanning the plaster patterns of teeth G. The second 3D image data of the present embodiment may include stereolithography (STL) data. The STL data may be in an ASCII or binary format and represents a surface of a 3D structure by a plurality of polygons in a 3D program so that modelling data of the 3D structure is easily recognized by a different type of a 3D program.

The data processing apparatus 130 receives and matches the first 3D image data and the second 3D image data, thereby generating the synthetic 3D image data.

The data processing apparatus 130 may include an input unit 131 for receiving an input of information from a user, an operation unit 132 for receiving the first 3D image data and the second 3D image data and generating the synthetic 3D image data, and a display unit 133 electrically connected to the operation unit 132 and visually displaying the synthetic 3D image data.

The input unit 131 is electrically connected to the operation unit 132, and receives an input of control information from the user and transmits the received control information to the operation unit 132.

The operation unit 132 receives the first 3D image data and the second 3D image data, generates the synthetic 3D image data, and visually displays the generated data on the display unit 133.

In other words, the synthetic 3D image data is generated through the organic interaction among the input unit 131, the display unit 133, and the operation unit 132. The generation of the synthetic 3D image data will be described in detail later.

After the generation of the synthetic 3D image data is completed, the position of the virtual implant K to be placed on the target patient on the synthetic 3D image data is determined. In this state, the user determines the position of the virtual implant K by overlapping the virtual implant K to be placed on the target patient over a plurality of positions on the synthetic 3D image data displayed on the display unit 133.

As such, the data obtained by overlapping the virtual implant K data on the synthetic 3D image data based on the synthetic 3D image data is referred to as the implant surgery planning data.

After generating the implant surgery planning data, the operation unit 132 of the present embodiment generates the information of interest that is part of the implant surgery planning data and transmits the generated information of interest to the server apparatus 200. The mobile device 300 receives the information of interest from the server apparatus 200 and displays the received information of interest.

The information of interest includes partial 3D image data that is data of a preset area around the virtual implant K of the implant surgery data. In other words, since a portion in which the user (dental doctor) is interested is information around the virtual implant K, the mobile linked implant diagnosis system of the present embodiment does not provide the whole of the implant surgery planning data to the mobile device 300, but provides only partial 3D image data that is 3D image data around the virtual implant K to the mobile device 300, due to a limit in the performance of a mobile device.

The partial 3D image data is the implant surgery planning data in the boundary area spaced apart by a preset distance from the center of the virtual implant K. In the present embodiment, the boundary area of the partial 3D image data is provided in a hexahedral shape as illustrated in detail in FIG. 10.

The boundary area in the hexahedral shape has a length a in a first axial direction of about 15 mm to about 45 mm, a length b in a second axial direction of about 15 mm to about 45 mm, and a length c in a third axial direction of about 20 mm to about 60 mm The mobile device 300 is connected to the server apparatus 200 in a wired or wireless manner, and receives the information of interest from the server apparatus 200 and display the received information of interest. In the present embodiment, the mobile device 300 may include smartphones, iPads, handheld terminals, etc., but the present disclosure is not limited thereto and various handheld electronic devices including a display unit, a communication unit, and an input unit may be used as the mobile device 300 of the present embodiment.

The mobile device 300 may include a mobile device display unit 310 for displaying the partial 3D image data, a mobile device input unit (not shown) for receiving an input of information from the user, a mobile device operation unit (not shown) electrically connected to the mobile device input unit and correcting the partial 3D image data according to the information input from the user, and a mobile device communication unit (not shown) for receiving the information of interest from the server apparatus 200 and transmitting the information of interest corrected by the user to the server apparatus 200.

Figure 13:
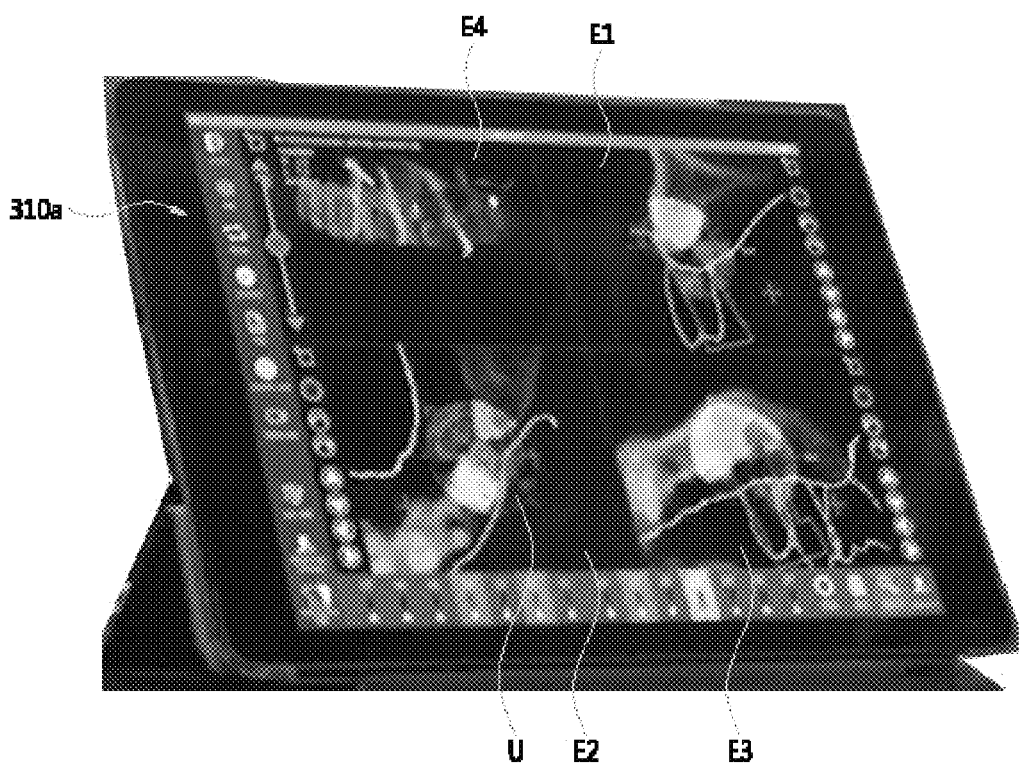
FIG. 13 is a screen displayed in the mobile device of a mobile linked implant diagnosis system according to another embodiment.

The mobile device display unit displays the partial 3D image data. In the mobile device display unit 310, as illustrated in FIGS. 11 to 13, a screen provided to the user is sectioned into a plurality of divided areas E1, E2, E3, and E4.

In the present embodiment, the divided areas may include a first area E1 in which a plane image obtained by cutting the partial 3D image data along a first axis and a second axis crossing the first axis is displayed, a second area E2 in which a plane image obtained by cutting the partial 3D image data along the second axis and a third axis crossing the second axis is displayed, a third area E3 in which a plane image obtained by cutting the partial 3D image data along the first axis and the third axis is displayed, and a fourth area E4 in which 3D image data obtained by overlapping the virtual implant K on the second 3D image data obtained by scanning the plaster patterns of teeth of the target patient is displayed.

The data visually displayed in the fourth area E4 is the 3D image data obtained by overlapping the virtual implant K on the second 3D image data obtained by scanning the plaster patterns of teeth of the target patient. This comprehensively shows the position where the virtual implant K is to be placed. Since the display is processed based on the second 3D image data, not the first 3D image data of a large capacity, a data transmission amount may be reduced.

The data visually displayed in the fourth area E4 is to facilitate the user to intuitively recognize the position of the virtual implant K in the mouth of the target patient.

In the first to third areas E1 to E3, an X-Y section, a Y-Z section, and an X-Z section at the center point of the partial 3D image data, mainly the center point of the virtual implant K, are respectively displayed.

When the first to third areas E1 to E3 display the sections of the partial 3D image data as above, the user may change an implant placement angle or finely move the position of an implant in an area through an input device such as a touch screen.

In the present embodiment, the sections of the partial 3D image data displayed in the first to third areas E1 to E3 are changed interlinked with one another. When the user changes the position of an implant in an area, images in the other areas are changed accordingly.

When changing the position and angle of an implant, the user checks bone density at a position where the implant is to be placed.

Accordingly, the mobile device display unit 310 of the present embodiment, as illustrated in detail in FIG. 12, visually displays bone density in the first to third areas E1 to E3. The bone density is displayed in different colors according to a value of the bone density.

Furthermore, in the present embodiment, a color displayed in the mobile device display unit 310 according to the value of the bone density is a chromatic value. As such, since the mobile device display unit 310 of the present embodiment displays the bone density displayed in the first to third areas E1 to E3 in different chromatic colors according to the value of the bone density, the user may intuitively recognize the bone density around the virtual fixture.

In the present embodiment, a high bone density value is displayed in yellow or green and a low bone density value is displayed in red or blue, but the present disclosure is not limited thereto and the bone density value may be displayed in various different colors.

In addition to the finely changing the position and angle of the placement of an implant, the user (dental doctor) may change a type of the virtual implant K, for example, a type of a fixture, an abutment, etc., in the partial 3D image data.

After a correction of changing the position and angle of the placement of an implant and a correction of changing the type of an implant are completed, the user stores results of the corrections and then the corrected partial 3D image data is transmitted to the server apparatus 200 and stored therein.

As such, in the mobile linked implant diagnosis system according to the present embodiment, since only the partial 3D image data of the implant surgery data, which is the 3D image data around the virtual implant K, is provided to the mobile device 300, the user may correct the partial 3D image data around the virtual implant K that is a user's main interest, for example, a correction of changing one fixture to another, a correction of finely changing an implant placement angle, etc., through the mobile device 300 within the specifications of the mobile device 300.

In the following description, an operation of generating the implant surgery planning data in the implant diagnosis apparatus 100 that generates the implant surgery planning data is described.

In order to generate the implant surgery planning data, it is necessary to first generate the synthetic 3D image data. The operation of generating the synthetic 3D image data is briefly described below.

The first 3D image data acquired from the first image information acquirement apparatus 110 such as a CT apparatus has a merit of enabling the accurate identification of a bone shape of a target patient. However, an image may be distorted by variously shaped prostheses and implants provided in the mouth of the target patient.

Accordingly, the synthetic 3D image data is generated, in which the second 3D image data containing very accurate information about the internal structure of the mouth of the target patient, which is acquired by scanning the plaster patterns of teeth G of the target patient, and the first 3D image data containing accurate information about the bone shape of the target patient are overlapped. An operation of matching the first 3D image data and the second 3D image data is needed to overlap the first 3D image data and the second 3D image data.

The operation of matching the first 3D image data and the second 3D image data may include a pre-matching operation of pre-matching the first 3D image data and the second 3D image data based on the coordinate of the matching reference marker G2 of the second 3D image data, and a precise matching operation of precisely matching the second 3D image data with the first 3D image data in the pre-matched synthetic 3D image data.

The pre-matching operation is a method of substantially fast matching the first 3D image data and the second 3D image data. In the pre-matching operation, the first 3D image data and the second 3D image data are pre-matched based on the coordinate of the matching reference marker G2 of the second 3D image data.

In the pre-matching operation, the user is provided with a screen as illustrated in FIGS. 6 and 7 through the screen of the display unit 133. The screen may include a teeth area display zone Z1 in which a teeth area of the target patient of the first 3D image data is visually displayed, a second 3D image data display zone Z2 in which the second 3D image data is visually displayed, and a synthetic 3D image data display zone Z3 in which the synthetic 3D image data is visually displayed.

The teeth area of the target patient of the first 3D image data is visually displayed in the teeth area display zone Z1. The teeth area of the target patient of the first 3D image data that is visually displayed in the teeth area display zone Z1 may be selected by a control signal through the input unit 131 by the user.

Furthermore, the second 3D image data is visually displayed in the second 3D image data display zone Z2. The synthetic 3D image data is visually displayed in the synthetic 3D image data display zone Z3.

In a screen of the display unit 133 of FIG. 6, the user inputs to the operation unit 132 the coordinate of the matching reference marker G2 in the second 3D image data display zone Z2. In other words, when the user clicks three matching reference markers G2 displayed in the second 3D image data display zone Z2 through the input unit 131 such as a mouse or the like, a clicked coordinate is transmitted to the operation unit 132.

Then, the user inputs a virtual coordinate corresponding to the coordinate of the matching reference marker G2 in the teeth area display zone Z1 to the operation unit 132. In other words, when the user compares an image of a teeth area displayed in the teeth area display zone Z1 and an image of the plaster patterns of teeth G displayed in the second 3D image data display zone Z2 and clicks a virtual position corresponding to the matching reference marker G2 in an image of the teeth area displayed in the teeth area display zone Z1, the clicked coordinate is transmitted to the operation unit 132.

Then, the operation unit 132 compares the input coordinate of the matching reference marker G2 and the input virtual coordinate, overlaps the first 3D image data and the second 3D image data, and displays in the synthetic 3D image data display zone Z3 pre-matched synthetic 3D image data obtained by overlapping the first 3D image data and the second 3D image data.

While the synthetic 3D image data display zone Z3 of FIG. 6 displays only the first 3D image data because the user's input of a coordinate is not performed, the synthetic 3D image data display zone Z3 of FIG. 7 displays synthetic 3D image data in which the second 3D image data is pre-matched with the first 3D image data as the coordinate of the matching reference marker G2 and the virtual coordinate corresponding to the coordinate of the matching reference marker G2 are input.

Since the pre-matching operation is performed as the user compares the image of the teeth area display zone Z1 and the image of the second 3D image data display zone Z2 and clicks a virtual position corresponding to the matching reference marker G2 in the image of the teeth area display zone Z1, although a degree of matching of the pre-matched synthetic 3D image data passing through the pre-matching operation is not in a perfect state, the pre-matched synthetic 3D image data passing through the pre-matching operation is in an almost matched state.

Accordingly, in the precise matching operation, in the pre-matched synthetic 3D image data in the almost matched state, the second 3D image data is precisely matched with the first 3D image data.

In the precise matching operation, a screen as illustrated in FIGS. 8 to 9 is provided to the user on the screen of the display unit 133. In other words, a plurality of divided zones D1, D2, D3, D4, D5, and D6 are displayed on the screen provided to the user through the display unit 133 in the precise matching operation. Different plane images of the pre-matched synthetic 3D image data are arranged in the divided areas D1, D2, D3, D4, D5, and D6.

In this state, the plane images of the pre-matched synthetic 3D image data displayed in the divided areas D1, D2, D3, D4, D5, and D6 may be distinguished by the first 3D image data and the second 3D image data (for example, outlines of the first 3D image data and the second 3D image data are displayed in different colors) so that the user may visually recognize whether the data is matched or not.

As illustrated in FIG. 8 or 9, in the precise matching operation of the present embodiment, a display area of the screen provided to the user through the display unit 133 is sectioned into the first to sixth divided areas D1, D2, D3, D4, D5, and D6.

The first divided area D1 is a plane of the pre-matched synthetic 3D image data and corresponds to a user's operation screen. In the present embodiment, the first divided area D1 displays an image of the pre-matched synthetic 3D image data cut by a plane of X-Y axes.

Three movement points M1, M2, and M3 are displayed in the first divided area D1. When the user moves an input point through the input unit 131 such as a mouse or the like, images of the second to sixth divided areas D2, D3, D4, D5, and D6 are changed.

The second divided area D2 displays an image cut by a plane of Y-Z axes at the position of the first movement point M1 of the first divided area D1. The third divided area D3 displays an image cut by a plane of the X-Z axes at the position of the first movement point M1 of the first divided area D1.

The images of the second divided area D2 and the third divided area D3 are changed to plane images at the position of the first movement point M1 moved along the movement of the first movement point M1 of the first divided area D1.

The fourth divided area D4 displays an image cut by the plane of the Y-Z axes at the second movement point M2 of the first divided area D1. The fifth divided area D5 displays an image cut by the plane of the X-Z axes at the position of the second movement point M2 of the first divided area D1.

The images of the fourth divided area D4 and the fifth divided area D5 are changed to plane images at the position of the second movement point M2 moved along the movement of the second movement point M2 of the first divided area D1.

The sixth divided area D6 displays an image cut by the plane of the Y-Z axes at the position of the third movement point M3 of the first divided area D1. The image of the sixth divided area D6 is changed to a plane image at the position of the third movement point M3 moved along the movement of the third movement point M3 of the first divided area D1.

In comparison of FIG. 8 and FIG. 9, it may be seen that the images of the second to sixth divided areas D2, D3, D4, D5, and D6 are changed according to the change in the positions of the first to third movement points M1, M2, and M3.

The images of the second to sixth divided areas D2, D3, D4, D5, and D6 are affected by the user's operation through the input unit 131. In other words, the images of the position and pose of the second 3D image data displayed in the second to sixth divided areas D2, D3, D4, D5, and D6 may be changed by the user's operation.

Accordingly, while moving the first to third movement points M1, M2, and M3, the user checks whether the first 3D image data and the second 3D image data are matched with each other at many positions in the plane image of the pre-matched synthetic 3D image data. Then, the user moves the second 3D image data relative to the first 3D image data through the input unit 131 to precisely match the first 3D image data and the second 3D image data.

As described above, since the outlines of the plane images displayed in the first to sixth divided areas D1, D2, D3, D4, D5, and D6 are expressed in different colors so that the first 3D image data and the second 3D image data may be distinguished, the user may precisely match the first 3D image data and the second 3D image data by clicking the second 3D image data through the input unit 131 such as a mouse and then dragging the clicked data.

The information about a precise matching state in which the user precisely matches an image of the second 3D image data to an image of the first 3D image data by using the input unit 131 is input to the operation unit 132. The operation unit 132 generates precisely matched synthetic 3D image data by correcting the pre-matched synthetic 3D image data according to the information about a precise matching state input by the input unit 131.

After generating the precisely matched synthetic 3D image data, the operation unit 132 overlaps the second 3D image data on the first 3D image data and replaces a portion of the first 3D image data, which corresponds to the second 3D image data, with the second 3D image data, thereby generating final synthetic 3D image data.

When the generation of the above synthetic 3D image data is completed, a position of a fixture P to be placed to the target patient is determined from the synthetic 3D image data. In this state, the user determines the position of the fixture P by overlapping the virtual fixture P to be placed to the target patient on various positions of the synthetic 3D image data displayed on the display unit 133.

When the virtual fixture P to be placed to the target patient overlaps the synthetic 3D image data, the data processing apparatus 130 of the present embodiment visually displays bone density around the virtual fixture P with respect to the virtual fixture P.

In other words, in the present embodiment, when the virtual fixture P to be placed to the target patient overlaps the synthetic 3D image data, the operation unit 132 calculates bone density around the virtual fixture P with respect to the virtual fixture P.

In the present embodiment, the bone density around the virtual fixture P refers to the bone density of an area in contact with an outer contour of the virtual fixture P, that is, the bone density of a portion of the fixture P where the outline of a thread of the fixture P is located.

The display unit 133 is electrically connected to the operation unit 132 and visually displays the synthetic 3D image data, for example, in a 2D plane image and a 3D image. The display unit 133 may display not only the synthetic 3D image data, but also the first 3D image data and the second 3D image data, as a visual image.

Furthermore, the display unit 133 of the present embodiment visually displays the bone density around the virtual fixture P based on the virtual fixture P calculated in the operation unit 132.

In other words, the display unit 133, as illustrated in FIGS. 3 and 4, visually displays the bone density of an area in contact with the outer contour of the virtual fixture P calculated in the operation unit 132. In the present embodiment, the bone density around the virtual fixture P display on the display unit 133 may be displayed in different colors according to a value of the bone density.

Furthermore, in the present embodiment, the color display on the display unit 133 according to the value of the bone density is a chromatic color. As such, in the mobile linked implant diagnosis system of the present embodiment, since the bone density around the virtual fixture P is displayed in different chromatic colors according to the value of the bone density, the user may be intuitively recognize the bone density around the virtual fixture P.

In the present embodiment, a high bone density value is displayed in yellow or green and a low bone density value is displayed in red or blue, but the present disclosure is not limited thereto and the bone density value may be displayed in various different colors.

The operation of the mobile linked implant diagnosis system of the present embodiment is described below with reference to FIGS. 1 to 12.

When the mobile device 300 is operated after receiving the partial 3D image data from the server apparatus 200, an image such as FIG. 11 is displayed on the screen of the mobile device 300.

When the first to third areas E1 to E3 display the sections of the partial 3D image data as illustrated in FIG. 11, the user may change an implant placement angle or finely move the position of an implant in an area through an input device such as a touch screen.

In the present embodiment, the sections of the partial 3D image data displayed in the first to third areas E1 to E3 are changed interlinked with one another. When the user changes the position of an implant in an area, images in the other areas are changed accordingly.

In addition to the finely changing the position and angle of the placement of an implant, the user (dental doctor) may change a type of the virtual implant K, for example, a type of a fixture, an abutment, etc., in the partial 3D image data.

After a correction of changing the position and angle of the placement of an implant and a correction of changing the type of an implant are completed, the user stores results of the corrections and then the corrected partial 3D image data is transmitted to the server apparatus 200 and stored therein.

Then, the user may receive in the mobile device 300 the corrected partial 3D image data stored in the server apparatus 200 and review the received corrected partial 3D image data again.

As such, in the mobile linked implant diagnosis system according to the present embodiment, since only the partial 3D image data of the implant surgery data, which is the 3D image data around the virtual implant K, is provided to the mobile device 300, the user may correct the partial 3D image data around the virtual implant K that is a user's main interest, for example, a correction of changing one fixture to another, a correction of finely changing an implant placement angle, etc., through the mobile device 300 within the specifications of the mobile device 300.

In the following description, an operation of generating the implant surgery planning data in the implant diagnosis apparatus 100 that generates the implant surgery planning data is described.

In order to generate the implant surgery planning data, it is necessary to first generate the synthetic 3D image data. A method of generating the synthetic 3D image data is briefly described below.

The method of generating an image for implant diagnosis of the mobile linked implant diagnosis system according to the present embodiment may include, as illustrated in FIG. 5, a first image information acquirement operation S110 of acquiring the first 3D image data about the mouth area of the target patient, a second image information acquirement operation S120 of acquiring the second 3D image data by scanning the plaster patterns of teeth G of the target patient, a synthetic 3D image data acquirement operation S130 of generating the synthetic 3D image data by matching the first 3D image data and the second 3D image data, and a bone density display operation S140 of visually displaying the bone density around the virtual fixture P based on the virtual fixture P when the synthetic 3D image data is overlapped with the virtual fixture P to be placed to the target patient.

In the first image information acquirement operation S110, the first 3D image data about the mouth area of the target patient is acquired. In the first image information acquirement operation S110, as illustrated in FIG. 1, the first image information acquirement apparatus 110 captures an image of the mouth area of a target patient to acquire the first 3D image data.

In the second image information acquirement operation S120, the second image information acquirement apparatus 120 scans the plaster patterns of teeth G of the target patient to acquire the second 3D image data.

In detail, the second image information acquirement operation S120 of the present embodiment may include generating the plaster patterns of teeth G of the target patient, providing the matching reference marker G2 on the plaster patterns of teeth G of the target patient, and scanning the plaster patterns of teeth G provided with the matching reference marker G2.

In the providing of the matching reference marker G2, the matching reference marker G2 for matching the second 3D image data to the plaster patterns of teeth main body G1 of the target patient manufactured in the generating of the plaster patterns of teeth G is formed.

The matching reference marker G2 provided on the plaster patterns of teeth main body G1 is used as a reference coordinate for matching the first 3D image data and the second 3D image data in the synthetic 3D image data acquirement operation S130.

In the synthetic 3D image data acquirement operation S130, the synthetic 3D image data is generated by matching the first 3D image data and the second 3D image data.

The first 3D image data acquired from the first image information acquirement apparatus 110 such as the CT apparatus, compared to its merit of enabling the accurate identification of the bone shape of the target patient, may be problematic in that an image may be distorted by variously shaped prostheses and implants provided in the mouth of the target patient.

Accordingly, the synthetic 3D image data is generated in which the second 3D image data containing very accurate information about the internal structure of the mouth of the target patient, which is acquired by scanning the plaster patterns of teeth G of the target patient, and the first 3D image data containing accurate information about the bone shape of the target patient are overlapped, and the matching operation that is essentially performed for the overlapping of the first 3D image data and the second 3D image data is performed in the synthetic 3D image data acquirement operation S130.

The synthetic 3D image data acquirement operation S130 may include a pre-matching operation S131 of pre-matching the first 3D image data and the second 3D image data based on the coordinate of the matching reference marker G2 of the second 3D image data, and a precise matching operation S132 of precisely matching the second 3D image data to the first 3D image data in the pre-matched synthetic 3D image data.

The pre-matching operation S131 is a method of substantially fast matching the first 3D image data and the second 3D image data. In the pre-matching operation S131, the first 3D image data and the second 3D image data are pre-matched based on the coordinate of the matching reference marker G2 of the second 3D image data.

The pre-matching operation S131 may include sectioning a display area of the screen provided to the user into the teeth area display zone Z1 in which a teeth area of the target patient of the first 3D image data is visually displayed, the second 3D image data display zone Z2 in which the second 3D image data is visually displayed, and the synthetic 3D image data display zone Z3 in which the synthetic 3D image data is visually displayed, a reference marker coordinate input operation of inputting the coordinate of the matching reference marker G2 in the second 3D image data display zone Z2, a virtual coordinate input operation of inputting the virtual coordinate corresponding to the coordinate of the matching reference marker G2 in the teeth area display zone Z1, and displaying the pre-matched synthetic 3D image data in the synthetic 3D image data display zone Z3 by matching the input coordinate of the matching reference marker G2 and the input virtual coordinate.

The pre-matching operation S131 is described below with reference to FIGS. 6 and 7. As illustrated in FIG. 6, the display area of a screen provided to the user through the display unit 133 is sectioned into the teeth area display zone Z1 in which the teeth area of the target patient of the first 3D image data is visually displayed, the second 3D image data display zone Z2 in which the second 3D image data is visually displayed, and the synthetic 3D image data display zone Z3 in which the synthetic 3D image data is visually displayed.

In the teeth area display zone Z1, the teeth area of the target patient of the first 3D image data is visually displayed. The teeth area of the target patient displayed in the teeth area display zone Z1 may be selected according to the user's control signal input through the input unit 131.

Furthermore, the second 3D image data is visually displayed in the second 3D image data display zone Z2, and the synthetic 3D image data is visually displayed in the synthetic 3D image data display zone Z3.

Both of the teeth area of the target patient displayed in the teeth area display zone Z1 and the second 3D image data displayed in the second 3D image data display zone Z2 indicate the structure of the mouth area of a target patient. As described above, since the second 3D image data has more accurate information about the structure of the mouth area of the target patient, when the synthetic 3D image data is generated, the structure of the mouth area of the target patient of the first 3D image data is replaced with the second 3D image data. For this replacement, the first 3D image data and the second 3D image data are matched with each other through the reference marker coordinate input operation and the virtual coordinate input operation.

In the reference marker coordinate input operation, the coordinate of the matching reference marker G2 is input in the second 3D image data display zone Z2. In other words, when the user clicks three matching reference markers G2 displayed in the second 3D image data display zone Z2 by using the input unit 131 such as a mouse or the like, a clicked coordinate is transmitted to the operation unit 132.

In the virtual coordinate input operation, the virtual coordinate corresponding to the coordinate of the matching reference marker G2 is input in the teeth area display zone Z1. In other words, when the user compares an image of the teeth area displayed in the teeth area display zone Z1 and an image of the plaster patterns of teeth G displayed in the second 3D image data display zone Z2 and then clicks a virtual position corresponding to the position of the matching reference marker G2 on the image of the teeth area displayed in the teeth area display zone Z1, the clicked coordinate is transmitted to the operation unit 132.

Then, in the displaying of the pre-matched synthetic 3D image data, the coordinate of the matching reference marker G2 and the virtual coordinate input to the operation unit 132 are compared with each other to overlap the first 3D image data and the second 3D image data and thus the pre-matched synthetic 3D image data obtained by overlapping the second 3D image data to the first 3D image data is displayed in the synthetic 3D image data display zone Z3.

It may be seen that, while only the first 3D image data is displayed in the synthetic 3D image data display zone Z3 of FIG. 6 because the reference marker coordinate input operation and the virtual coordinate input operation are not performed yet, as the reference marker coordinate input operation and the virtual coordinate input operation are performed, an image of the synthetic 3D image data in which the second 3D image data is overlapped on first 3D image data is displayed in the synthetic 3D image data display zone Z3 of FIG. 7.

In the above-described virtual coordinate input operation of the pre-matching operation S131, since the user compares the image of the teeth area display zone Z1 and the image of the second 3D image data display zone Z2 and clicks a virtual position of the matching reference marker G2 on the image of the teeth area display zone Z1, although a degree of matching of the pre-matched synthetic 3D image data passing through the pre-matching operation S131 is not in a complete state, the pre-matched synthetic 3D image data passing through the pre-matching operation S131 is in an almost matched state.

Accordingly, in the precise matching operation S132, the second 3D image data is precisely matched to the first 3D image data in the pre-matched synthetic 3D image data of an almost matched state.

The precise matching operation S132 may include an operation of sectioning the display area of the screen provided to the user through the display unit 133 into a plurality of divided zones and arranging different plane images of the pre-matched synthetic 3D image data in the divided areas, and an operation of performing correction in each divided area such that the second 3D image data is matched to the first 3D image data.

As illustrated in FIG. 8 or 9, in the precise matching operation S132, the display area of the screen provided to the user through the display unit 133 is sectioned into a plurality of divided zones D1, D2, D3, D4, D5, and D6. Different plane images of the pre-matched synthetic 3D image data are arranged in the divided areas D1, D2, D3, D4, D5, and D6.

The different plane images of the pre-matched synthetic 3D image data arranged in the divided areas D1, D2, D3, D4, D5, and D6 is distinguished by the first 3D image data and the second 3D image data, for example, the outlines of the first 3D image data and the second 3D image data are displayed in different colors, so that the user may visually recognize whether the data is matched or not.

As illustrated in FIG. 8 or 9, in the precise matching operation S132, the display area of the screen provided to the user through the display unit 133 is sectioned into the first to sixth divided areas D1, D2, D3, D4, D5, and D6.

The first divided area D1 is a plane of the pre-matched synthetic 3D image data and corresponds to a user's operation screen. In the present embodiment, the first divided area D1 displays an image of the pre-matched synthetic 3D image data cut by the plane of the X-Y axes.

Three movement points M1, M2, and M3 are displayed in the first divided area D1. When the user moves an input point through the input unit 131 such as a mouse or the like, images of the second to sixth divided areas D2, D3, D4, D5, and D6 are changed.

The second divided area D2 displays an image cut by the plane of the Y-Z axes at the position of the first movement point M1 of the first divided area D1. The third divided area D3 displays an image cut by the plane of the X-Z axes at the position of the first movement point M1 of the first divided area D1.

The images of the second divided area D2 and the third divided area D3 are changed to plane images at the position of the first movement point M1 moved along the movement of the first movement point M1 of the first divided area D1.

The fourth divided area D4 displays an image cut by the plane of the Y-Z axes at the second movement point M2 of the first divided area D1. The fifth divided area D5 displays an image cut by the plane of the X-Z axes at the position of the second movement point M2 of the first divided area D1.

The images of the fourth divided area D4 and the fifth divided area D5 are changed to plane images at the position of the second movement point M2 moved along the movement of the second movement point M2 of the first divided area D1.

The sixth divided area D6 displays an image cut by the plane of the Y-Z axes at the position of the third movement point M3 of the first divided area D1. The image of the sixth divided area D6 is changed to a plane image at the position of the third movement point M3 moved along the movement of the third movement point M3 of the first divided area D1.

In comparison of FIG. 8 and FIG. 9, it may be seen that the images of the second to sixth divided areas D2, D3, D4, D5, and D6 are changed according to the change of the positions of the first to third movement points M1, M2, and M3.

The images of the second to sixth divided areas D2, D3, D4, D5, and D6 are affected by the user's operation through the input unit 131. In other words, the images of the position and pose of the second 3D image data displayed in the second to sixth divided areas D2, D3, D4, D5, and D6 may be changed by the user's operation.

Accordingly, while moving the first to third movement points M1, M2, and M3, the user checks whether the first 3D image data and the second 3D image data are matched with each other at many positions in the plane image of the pre-matched synthetic 3D image data. Then, the user moves the second 3D image data relative to the first 3D image data through the input unit 131 to precisely match the first 3D image data and the second 3D image data.

The user may control the scale of the first 3D image data through a scale control portion S displayed in the display area of the screen provided to the user through the display unit 133. The scale of the first 3D image data is controlled to further facilitate a precise matching operation of the first 3D image data and the second 3D image data by relatively varying the overall size of the first 3D image data with respect to the second 3D image data when there is a difference in the overall size between the first 3D image data and the second 3D image data.

As such, in the method of generating an image for implant diagnosis according to the present embodiment, since the first 3D image data and the second 3D image data are substantially fast pre-matched and then the pre-matched synthetic 3D image data is substantially precisely matched again, an overall matching time may be reduced and matching accuracy may be improved.

Next, after the synthetic 3D image data acquirement operation S130 is completed by performing the precise matching operation S132, the user establishes surgery planning. During the surgery planning, the bone density of an alveolar bone of the target patient is a very important factor, and the position, depth, and direction of placement of an implant are determined according to the state of the bone density of the target patient.

Accordingly, the bone density of an area where the fixture P is placed is very important. In the bone density display operation S140 of the present embodiment, the bone density of an area where the fixture P is placed is displayed very intuitively.

In other words, in the bone density display operation S140 of the present embodiment, as illustrated in FIGS. 3 and 4, by overlapping the virtual fixture P to be placed to the target patient to synthetic 3D image data, the bone density around the virtual fixture P is visually displayed based on the virtual fixture P.

In the bone density display operation S140, the bone density of an area in contact with the outer contour of the virtual fixture P calculated in the operation unit 132 is displayed in a different color according to the value of the bone density.

As such, in the method of generating an image for implant diagnosis in the mobile linked implant diagnosis system according to the present embodiment, since the bone density around the virtual fixture P is displayed in a different color according to the value of the bone density, the user may intuitively recognize the bone density around the virtual fixture P.

FIG. 13 is a screen displayed in the mobile device of a mobile linked implant diagnosis system according to another embodiment.

When compared to the above-described embodiment, the present embodiment is different in that a mobile device display unit 310a visually displays the bone density in a preset area U in the first to third areas. However, since the other structures of the present embodiment are the same as those of the above-described embodiment in FIGS. 1 to 12, descriptions on the redundant structures are omitted in the following description.

The mobile device display unit of the present embodiment visually displays the bone density in the preset area U in the first to third areas E1 to E3.

In the present embodiment, the preset area U is provided in a circular shape, as illustrated in FIG. 13, and may be moved in each of the first to third areas E1 to E3 in a manner of using a touch screen by a user's operation.

As such, in the mobile linked implant diagnosis system of the present embodiment, since a mobile device display unit 130a visually displays the bone density in the preset area U in the first to third areas E1 to E3, the user may intensively review the bone density of an area of interest.

As described above, according to the above-described embodiments, since only the information of interest that is part of the implant surgery planning data is provided to a mobile device and the information of interest includes the partial 3D image data of the implant surgery data, which is 3D image data around a virtual implant, the user may correct the partial 3D image data around the virtual implant that is a user's main interest, for example, a correction of changing one fixture to another, a correction of finely changing an implant placement angle, etc., through the mobile device within the specifications of the mobile device.

While the inventive concept has been particularly shown and described with reference to exemplary embodiments thereof, it will be understood that various changes in form and details may be made therein without departing from the spirit and scope of the following claims.

INDUSTRIAL APPLICABILITY

The present invention relates to mobile linked implant diagnosis system and can be used in medical industry, particularly, dental industry.

The invention claimed is:

1. A mobile linked implant diagnosis system comprising: an implant diagnosis apparatus acquiring synthetic three-dimensional (3D) image data about a mouth area of a target patient and generating implant surgery planning data, in which virtual implant data is overlapped on the synthetic 3D image data, based on the synthetic 3D image data, wherein the implant diagnosis apparatus comprises:
  a first image information acquirement apparatus acquiring first 3D image data about the mouth area of the target patient;
  a second image information acquirement apparatus acquiring second 3D image data by scanning plaster patterns of teeth of the target patient, wherein the plaster patterns of teeth are provided with a matching reference marker for matching the first 3D image data and the second 3D image data, and wherein the matching reference marker is provided plurally, and the plurality of matching reference markers are arranged spaced apart from one another; and
  a data processing apparatus receiving and matching the first 3D image data and the second 3D image data and generating the synthetic 3D image data, and generating surgery planning data based on the synthetic 3D image data, wherein the data processing apparatus comprises:
    an input unit receiving information from a user;
    an operation unit generating the synthetic 3D image data, electrically connected to the input unit, and correcting the synthetic 3D image data based on the information input from the user; and
    a display unit electrically connected to the operation unit and visually displaying the synthetic 3D image data,
  wherein the data processing apparatus generates the synthetic 3D image data by performing a pre-matching operation of pre-matching the first 3D image data and the second 3D image data based on a coordinate of the matching reference marker of the second 3D image data and then performing a precise matching operation of precisely matching the second 3D image data to the first 3D image data in the pre-matched synthetic 3D image data,
  wherein, in the precise matching operation, the operation unit:
    sections a display area of the display unit into a plurality of divided zones,
    arranges different plane images of the pre-matched synthetic 3D image data in the plurality of divided zones, and
    receives an input of a state of matching, in which the user precisely matches the second 3D image data to the first 3D image data in each divided zone through the input unit;
  a server apparatus connected to the implant diagnosis apparatus in a wired or wireless manner, and receiving information of interest that is a subset of the implant surgery planning data generated in the implant diagnosis apparatus and storing the information of interest; and
  a mobile device connected to the server apparatus in a wired or wireless manner, and receiving only the information of interest from the server apparatus and displaying the information of interest,
  wherein the information of interest comprises partial 3D image data of the implant surgery planning data, the partial 3D image data being data about a preset area around the virtual implant.

2. The mobile linked implant diagnosis system of claim 1, wherein the partial 3D image data comprises the implant surgery planning data in a boundary area spaced apart by a preset distance from a center of the virtual implant.

3. The mobile linked implant diagnosis system of claim 2, wherein the boundary area is provided in a hexahedral shape, and
  wherein the boundary area in a hexahedral shape has a length in a first axis direction of about 15 mm to about 45 mm, a length in a second axis direction of about 15 mm to about 45 mm, and a length in a third axis direction of about 20 mm to about 60 mm.

4. The mobile linked implant diagnosis system of claim 1, wherein the mobile device comprises a smartphone or a handheld terminal, and
  wherein the mobile device comprises:
  a mobile device display unit displaying the partial 3D image data;
  a mobile device input unit receiving an input of information from a user; and
  a mobile device operation unit electrically connected to the mobile device input unit and correcting the partial 3D image data according to information input from the user.

5. The mobile linked implant diagnosis system of claim 4, wherein the mobile device display unit sections a screen provided to the user into a plurality of divided areas, and the divided areas comprises:
  a first area, in which a plane image obtained by cutting the partial 3D image data along a first axis and a second axis crossing the first axis, is displayed;
  a second area, in which a plane image obtained by cutting the partial 3D image data along the second axis and a third axis crossing the second axis, is displayed; and
  a third area, in which a plane image obtained by cutting the partial 3D image data along the first axis and the third axis, is displayed.

6. The mobile linked implant diagnosis system of claim 5, wherein the mobile device display unit visually displays bone density in the first area to third area, and
  wherein the mobile device display unit visually displays bone density in a preset area in the first area to third area, and
  wherein the bone density is displayed in a different color according to a value of the bone density, and
  wherein the color is a chromatic color.

7. The mobile linked implant diagnosis system of claim 5, wherein the divided areas further comprises a fourth area in which 3D image data obtained by overlapping the virtual implant to second 3D image data acquired by scanning plaster patterns of teeth of the target patient is displayed.

8. The mobile linked implant diagnosis system of claim 1, wherein, in the pre-matching operation, the operation unit sections a display area of the display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed,
  receives an input of the coordinate of the matching reference marker in the second 3D image data display zone through the input unit,
  receives an input of a virtual coordinate corresponding to the coordinate of the matching reference marker in the teeth area display zone through the input unit, and
  displays the pre-matched synthetic 3D image data in the synthetic 3D image data display zone by matching the input coordinate of the matching reference marker G2 and the input virtual coordinate.

9. The mobile linked implant diagnosis system of claim 1, wherein the plurality of divided zones comprise:
  a first area in which a plane image obtained by cutting the pre-matched synthetic 3D image data along a first axis and a second axis crossing the first axis is displayed;
  a second area in which a plane image obtained by cutting the pre-matched synthetic 3D image data along the second axis and a third axis crossing the second axis at a position of a first movement point displayed in the first area is displayed;
  a third area in which a plane image obtained by cutting the pre-matched synthetic 3D image data along the first axis and the third axis at the position of the first movement point displayed in the first area is displayed;
  a fourth area in which a plane image obtained by cutting the pre-matched synthetic 3D image data along the second axis and the third axis at a position of a second movement point displayed in the first area is displayed;
  a fifth area in which a plane image obtained by cutting the pre-matched synthetic 3D image data along the first axis and the third axis at the position of the second movement point displayed in the first area is displayed; and
  a sixth area in which a plane image obtained by cutting the pre-matched synthetic 3D image data along the second axis and the third axis at a position of a third movement point displayed in the first area is displayed.

10. The mobile linked implant diagnosis system of claim 9, wherein the first to third movement points are movable by an operation of the user,
  the images of the second area and the third area are changed linked with a movement of the first movement point,
  the images of the fourth area and the fifth area are changed linked with a movement of the second movement point, and
  the image of the sixth area is changed linked with a movement of the third movement point.

11. The mobile linked implant diagnosis system of claim 1, wherein, when a virtual fixture to be placed in the target patient is overlapped on the synthetic 3D image data, the data processing apparatus visually displays bone density around the virtual fixture based on the virtual fixture.

12. The mobile linked implant diagnosis system of claim 11, wherein the data processing apparatus visually displays bone density of an area in contact with an outer contour of the virtual fixture, and
  wherein the bone density around the virtual fixture is displayed in a different color according to a value of the bone density.

* * * * *